US006663582B2

(12) United States Patent
Ballard et al.

(10) Patent No.: US 6,663,582 B2
(45) Date of Patent: Dec. 16, 2003

(54) WEARABLE MEDICATION VIAL HOLDER, AND VIAL FOR USE THEREWITH

(75) Inventors: Jerome Douglas Ballard, Tega Cay, SC (US); Carol Jeannette Ballard, Tega Cay, SC (US); Christopher George Lerra, Manchester, NH (US)

(73) Assignee: Cambridge Marketing, Inc., Rock Hill, SC (US)

( * ) Notice: Subject to any disclaimer, the term of this patent is extended or adjusted under 35 U.S.C. 154(b) by 0 days.

(21) Appl. No.: 10/004,391

(22) Filed: Oct. 25, 2001

(65) Prior Publication Data

US 2003/0083601 A1 May 1, 2003

(51) Int. Cl.⁷ .................................................. A61F 13/00
(52) U.S. Cl. ........................ 602/64; 602/78; 604/93.01; 604/174
(58) Field of Search .............................. 604/93.01, 174, 604/179, 304, 306, 308, 310, 311, 345, 327, 353, 332; 128/877, 878; 602/5, 20–21, 64, 78

(56) References Cited

U.S. PATENT DOCUMENTS

| 4,228,796 | A | * | 10/1980 | Gardiner |
| 5,098,399 | A | * | 3/1992 | Tollini |
| 5,171,214 | A | * | 12/1992 | Kolber et al. |
| 5,538,500 | A | * | 7/1996 | Peterson |
| 5,601,895 | A | * | 2/1997 | Cunningham |
| 5,897,519 | A | * | 4/1999 | Shesol et al. |
| 5,911,709 | A | * | 6/1999 | Hogan |
| 5,941,856 | A | * | 8/1999 | Kovacs et al. |
| 6,086,564 | A | * | 7/2000 | McLaughlin |

* cited by examiner

Primary Examiner—Nicholas D. Lucchesi
Assistant Examiner—Lalita M. Hamilton
(74) Attorney, Agent, or Firm—Alston & Bird LLP

(57) ABSTRACT

A wearable vial holder for securing at least one vial of medication on the person of a medical practitioner comprises a body-engaging member structured and arranged to be secured to a part of the body of a medical practitioner, and a vial gripper affixed to the body-engaging member for releasably grasping and holding at least one vial so that the practitioner has access to the vial(s) for one-handed drawing of medication therefrom using a syringe with a needle. The vial holder includes a needle-puncture-resistant shield to protect the practitioner against accidental needle sticks.

18 Claims, 3 Drawing Sheets

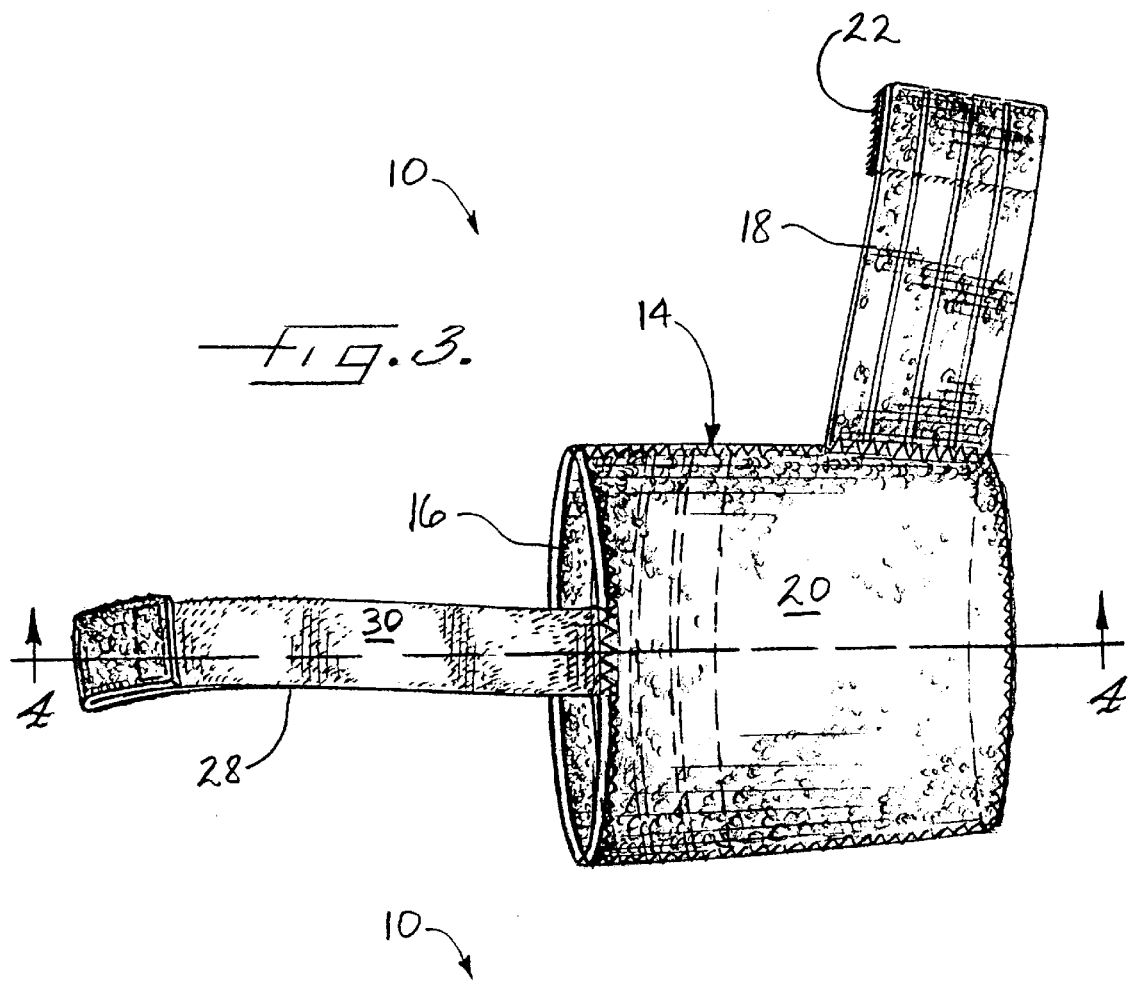

WEARABLE MEDICATION VIAL HOLDER, AND VIAL FOR USE THEREWITH

FIELD OF THE INVENTION

The present invention relates to devices facilitating the use of syringes and needles for injecting medication into a patient, and more specifically relates to a device enabling a single medical practitioner to hold a medication vial and draw medication therefrom with a syringe and needle using only one hand.

BACKGROUND OF THE INVENTION

Medical procedures performed in doctor offices and hospitals often require the injection of medication into a patient using a syringe and needle. For instance, it is frequently necessary, or at least desirable for the comfort of the patient, to inject a local anesthetic such as lidocaine into a part of the patient's body. It is standard procedure for a doctor or other medical practitioner to put on sterile gloves before touching or working on the patient to reduce the risk of introducing infectious microbes into the patient's body. It is also standard procedure for instruments that will be used upon the patient during a procedure, such as a needle and syringe used for injecting medications, to be sterilized before the procedure and to be laid out upon a sterile tray or the like. Proper protocol in order to preserve the sterile field calls for the doctor not to touch anything outside the sterile field once he or she has donned the sterile gloves and prior to touching the patient or any instrument that will be used on the patient.

The use of injectable medications complicates preservation of the sterile field because the outer surfaces of medication vials containing injectable medications are generally non-sterile. It is against protocol, therefore, for the medical practitioner to touch a medication vial with his or her gloved hands prior to working on a patient. Consequently, medical practitioners are forced to engage in all sorts of inefficient and/or potentially unsafe tactics simply to draw medication from a medication vial with a needle and syringe. The procedure cannot ordinarily be accomplished with one hand because the vial must be inverted (cap side down) while drawing medication into the syringe in order to prevent air from being drawn into the syringe, and the vial must be restrained to allow the needle to be pulled back out. One method that is commonly used is for the practitioner to call for an assistant to hold the medication vial while the practitioner inserts the needle into the vial and draws medication therefrom. If an assistant is not immediately available, the practitioner may be forced to wait until an assistant is free to come and assist. Thus, valuable time can be wasted, and meanwhile the patient may be in need of pain-relieving or other medication. Furthermore, it is possible for the practitioner to accidentally miss the vial and stick the assistant with the needle, which not only renders the needle non-sterile so that it must be discarded and replaced with a new sterile needle, but is also undesirable for the assistant, needless to say.

Another procedure that some medical practitioners use is to insert the needle into the vial while the vial is sitting upright on a table or the like, pick the vial up using only the inserted needle and syringe held in one hand, place the vial into the crook of the other arm, and grasp the vial between the upper arm and forearm. The practitioner then raises his or her arm to turn the vial cap side down so that medication can be drawn into the syringe, and then withdraws the needle from the vial. The practitioner then must put the vial back down on a table or other surface, using only his arm to maneuver the vial. If the vial is a multi-dose vial that is to be used again for the same patient, the vial must be set down on the table in an upright position so that the same procedure can be repeated when the practitioner needs to draw additional medication from the vial. It can be very difficult to set a vial down in an upright position using only one's arm holding the vial in the crook of the arm.

Thus, a need has long existed and continues to exist for a device enabling a medical practitioner to hold and maneuver medication vials and draw medication from the vials with a needle and syringe without having to touch or hold the vials with the hands.

SUMMARY OF THE INVENTION

The present invention addresses the above needs and achieves other advantages, by providing a wearable vial holder for securing at least one vial of medication on the person of a medical practitioner. The wearable vial holder comprises a body-engaging member structured and arranged to be secured to a part of the body of a medical practitioner, and a vial gripper affixed to the body-engaging member for releasably grasping and holding at least one vial so that the practitioner has access to the vial(s) for one-handed drawing of medication therefrom using a syringe with a needle.

In a preferred embodiment of the invention, the body-engaging member is configured to wrap securely about an arm of a medical practitioner so that it can be positioned, for example, on the forearm just below the elbow. However, the body-engaging member alternatively can be positioned on other parts of the body. The body-engaging member in preferred embodiments advantageously incorporates one or more elastic elements facilitating a secure, snug fit about the part of the body on which it is positioned, and preferably is also adjustable in size to fit people of varying sizes and proportions.

A preferred construction of the wearable vial holder employs a two-component releasable fastening system, such as a hook and loop (e.g., VELCRO®) system, providing releasable attachment between the body-engaging member and the vial gripper. In a preferred embodiment, the vial gripper comprises a strap or other gripping member that has one component of the releasable fastening system on a surface thereof, and the body-engaging member has the other component of the fastening system on its surface. Accordingly, the vial gripping member can be releasably attached to the body-engaging member such that a vial is gripped therebetween. The gripping member can be attached to the body-engaging member in various positions thereon, so as to accommodate various sizes and/or numbers of vials. If desired, one end of the gripping member can be permanently attached to the body-engaging member, such as by sewing or any other suitable technique.

The body-engaging member preferably incorporates a needle-puncture-resistant shield for covering the part of the body of the medical practitioner that is adjacent to a vial held in the vial gripper. In a preferred embodiment of the invention, the body-engaging member is a multi-layer construction including at least a shield layer and an outer layer whose outer surface has one component of the two-component releasable fastening system. For example, the outer surface of the outer layer can be formed by a loop component of a hook and loop fastening system. The body-engaging member can also include an inner layer that lies against the body part of the practitioner and that is breathable for comfort.

Preferably, a vial for use with the wearable vial holder has an attachment member affixed to it. The attachment member on the vial preferably comprises a component of the releasable two-component fastening system, which works in cooperation with the other component of the fastening system disposed on the outer surface of the body-engaging member, in order to releasably affix the vial to the body-engaging member. The attachment member on the vial allows the vial to be secured in place on the body-engaging member so that the practitioner's hand is then free to operate the vial gripper, which preferably comprises a strap or the like having the same component of the fastening system that is on the vial. In exemplary embodiments of the invention, the vial has a patch of hook material of a hook and loop fastening system attached to it, the vial gripper also has hook material, and the body-engaging member's outer surface has a loop component of the fastening system. However, various arrangements of the fastening system components can be used in accordance with the present invention, and furthermore other types of fastening systems besides hook and loop systems can alternatively be used. For instance, one or more vials can be releasably affixed to the body-engaging member by frictional grippers (e.g., resilient fingers that grip a vial snapped into place between the fingers) provided on the body-engaging member, or a movable clamp arrangement can be provided on the body-engaging member for releasably clamping a vial. Other vial-gripping devices are also possible within the scope of the present invention.

In accordance with the invention, a medical practitioner would don the wearable vial holder, and would install in the vial holder the vial or vials he or she anticipated using in a particular procedure. The practitioner would then put on sterile gloves. From that point on, the practitioner is able to draw medication from the vial(s) without having to pick up or touch the vial(s). Thus, the invention eliminates the requirement of an assistant to hold vials, along with the attendant risk of accidentally sticking the assistant with a needle. The invention thus facilitates a substantial savings in time (and, hence, expense), since the practitioner does not have to wait until an assistant becomes available in order to draw medication from a vial, and enables existing staff to be used in a safer and more-efficient manner.

BRIEF DESCRIPTION OF THE DRAWINGS

The above and other objects, features, and advantages of the invention will become more apparent from the following description of certain preferred embodiments thereof, when taken in conjunction with the accompanying drawings in which:

FIG. 3 is a perspective view of the vial holder in isolation;

FIG. 4 is a cross-sectional view taken along line 4—4 in FIG. 3; and

DETAILED DESCRIPTION OF THE INVENTION

Figure 1:
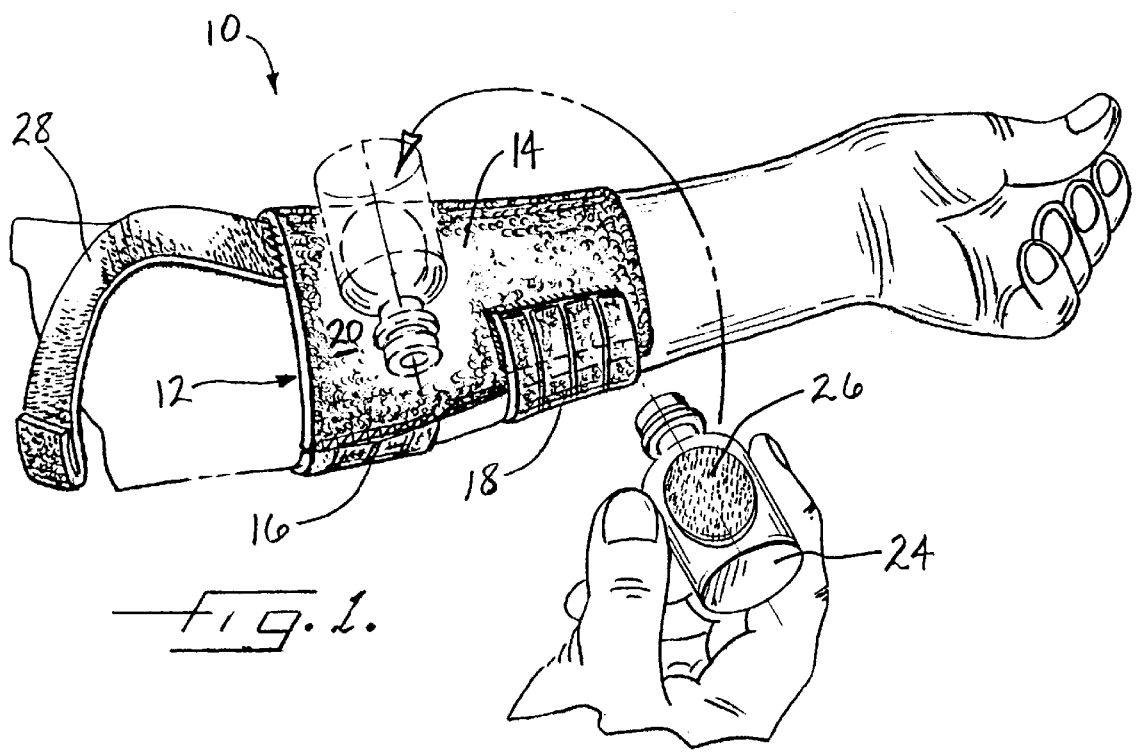
FIG. 1 is a perspective view showing a medical practitioner wearing a medication vial holder in accordance with the invention and placing a vial into the holder.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

With reference to the drawings, a wearable medication vial holder 10 in accordance with a preferred embodiment of the invention is illustrated. The vial holder 10 includes a body-engaging member 12 for encircling an arm of a medical practitioner. More particularly, the body-engaging member 12 includes a base 14 sized to only partially encircle an average-sized arm just below the elbow, a first elastic member 16 having its opposite ends affixed to opposite edges of the base 14, and a second elastic member 18 having one end affixed to one edge of the base 14. The base 14 and first elastic member 16 together form a band or sleeve for encircling the arm, and the elastic member 16 can elastically stretch to accommodate various arm sizes and remain snug about the arm. The second elastic member 18 provides further size adjustment capability and additional gripping strength about the arm, as further described below.

The outward-facing or outer surface of the base 14 is formed in whole or in part of a first component 20 of a two-component releasable fastening system. A preferred fastening system comprises any of the various hook and loop fastening systems available from Velcro USA Inc. of Manchester, N.H. under the trademark VELCRO®, or the hook and loop fastening systems available from Velcro USA Inc. that employ hook components sold under the trademark ULTRA-MATE®. However, other types of releasable fastening systems can be used instead. The first component 20 preferably comprises a loop component of the hook and loop fastening system. A loop component generally comprises a fabric formed to have a large number of thread loops exposed at its surface for engaging hooks of the hook component of the system. Preferably, substantially the entire outer surface of the base 14 of the vial holder is formed of the loop component 20. Additionally, it is preferred to have loop material on the outer surface of the first elastic member 16 as well, for reasons explained below.

The second elastic member 18 at its free end has a region of its inner surface covered by the second component of the releasable fastening system. Thus, in the preferred embodiment comprising hook and loop fasteners, the second elastic member 18 has a piece of hook material 22 attached to the inner surface of the elastic member at the free end thereof. Accordingly, the free end of the elastic member 18 can be releasably attached to the outer surface of the base 14 by engaging the hook material 22 on the member with the loop material 20 on the base 14, as shown in FIG. 1. The hook material 22 can extend as far along the length of the elastic member 18 toward the fixed end thereof as needed to provide a secure releasable attachment of the free end of the member to the outer surface of the base 14. The snugness of the fit of the vial holder 10 about one's arm can be adjusted by attaching the second elastic member 18 in various locations on the outer surface of the base 14 to make the relaxed circumference of the vial holder larger or smaller; to this end, as noted above, it is advantageous to have loop material 20 covering most or all of the outer surface of the base 14. Additionally, it is advantageous but not essential to have loop material 20 on the outer surface of the first elastic member 16 so that the second elastic member can be attached to it, if desired.

Figure 2:
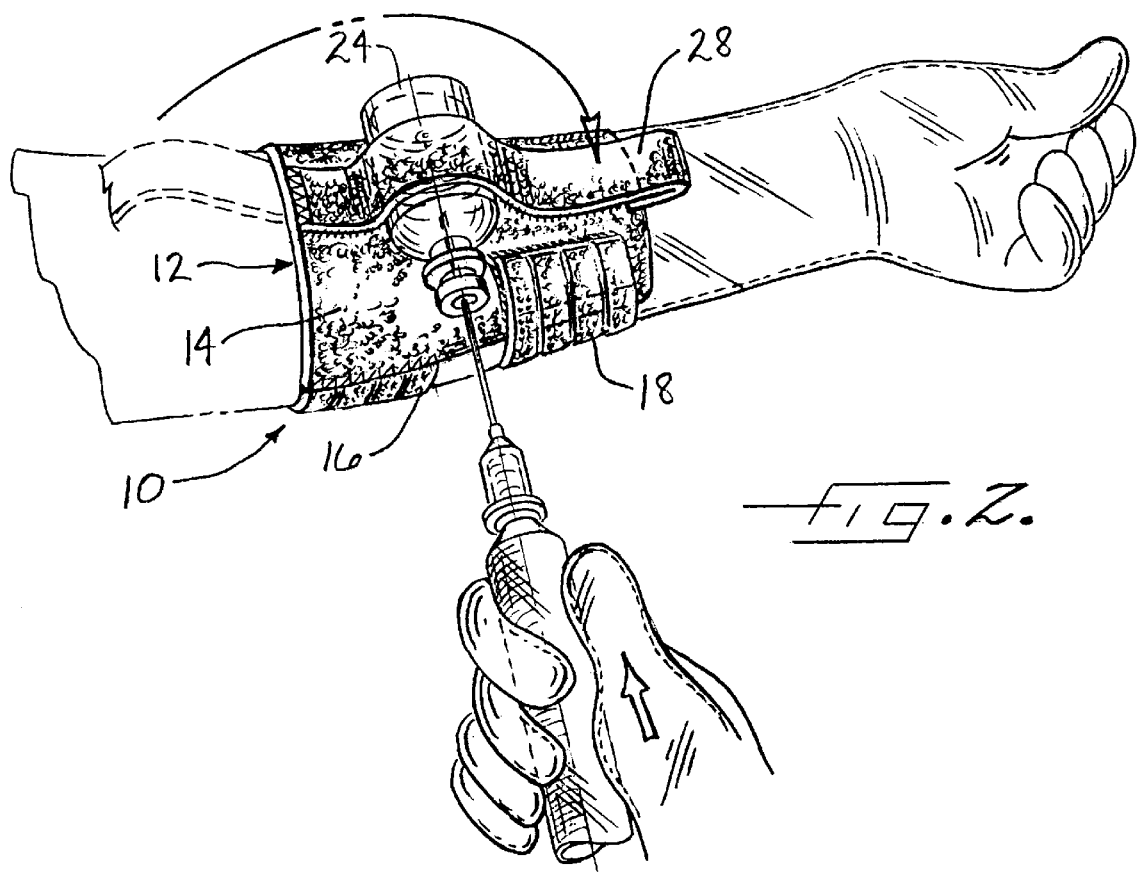
FIG. 2 is a view similar to FIG. 1, showing the vial secured in the holder and showing the medical practitioner inserting a needle into the vial in preparation for drawing medication from the vial into a syringe attached to the needle.

To secure a vial 24 in the vial holder 10, preferably the vial has a patch of hook material 26 affixed to it. Thus, the vial 24 can be releasably attached to the outer surface of the base 14 by engaging the hook patch 26 with the loop material 20 on the outer surface of the base 14. However, the attachment force provided by the hook patch 26 on the vial is insufficient to withstand the types of forces exerted on the vial during use without the vial becoming detached from the vial holder; rather, the hook patch 26 is provided so that the vial can be fixed in place on the base 14 to allow the practitioner to then operate a vial gripping strap 28 for securing the vial in the vial holder. The vial gripping strap 28 has one end affixed to the base 14 such as by stitching or other substantially permanent attachment method. The strap 28 has hook material 30 forming its inner surface such that the strap is releasably attachable to the outer surface of the base 14. To secure the vial 24, the strap 28 is drawn over the top of the vial and attached to the base 14 so that the vial is clamped between the strap 28 and the base 14, as shown in FIG. 2. The strap 28 can be formed of a material that has hooks on one side for engaging the loop material on the base 14, and loops on the opposite side. An end portion of the strap can be folded over and stitched or otherwise secured, as shown in FIG. 4, so as to form a tab portion on the end of the strap that will not adhere to the loop material on the base 14. This facilitates getting a grasp on the strap to detach it from the base 14.

Once the vial is secured in the vial holder, the medical practitioner can put on sterile gloves and use one hand to insert a needle into the vial as shown in FIG. 2, and draw medication from the vial. The vial can easily be inverted by raising the arm having the vial holder so that medication can be drawn without drawing air into the syringe. The practitioner can then inject the patient and carry on with other activities and procedures, while the vial 24 is still held in the vial holder 10. If the patient requires a second injection of medication from the same vial 24, the practitioner can draw further medication from the vial when the vial is a multi-dose vial.

Figure 5:
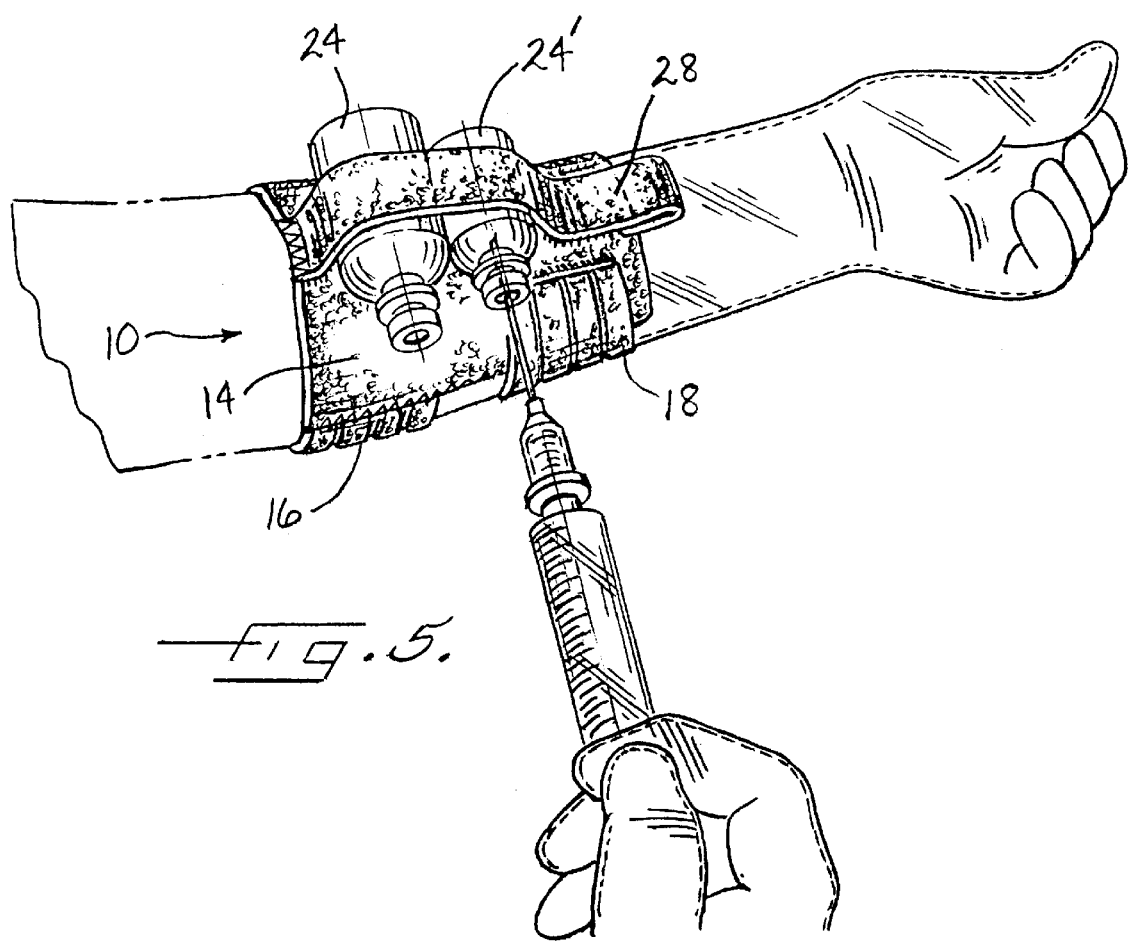
FIG. 5 is a perspective view showing two vials secured in the vial holder and showing a medical practitioner drawing medication from one of the vials.

In some cases, the practitioner may anticipate requiring more than one type of injectable medication for a particular patient or procedure. The vial holder 10 thus is preferably sized and configured to hold more than one vial 24, 24', as shown in FIG. 5. Various sizes of vials can be held in the vial holder. In a preferred embodiment of the invention, the vial holder is sized and configured to hold vials containing from about 10 to 50 ml of liquid medication, which are commonly available. However, the vial holder can be sized and configured to hold larger vials, if desired.

It is possible that when attempting to insert a needle into a vial held in the vial holder 10, the practitioner may accidentally miss the vial and stick the base 14 of the vial holder. Accordingly, the base 14 preferably includes a needle-puncture-resistant shield 32 to prevent a needle from piercing entirely through the base 14 into the practitioner's arm. The shield 32 may comprise, for example, a flexible sheet of plastic or other material that is puncture-resistant but sufficiently flexible to enable the vial holder to be wrapped about an arm. In the preferred embodiment, the base 14 of the vial holder comprises a multi-layer structure, including the shield 32, an outer layer 34 whose outer surface has the loop material 20, and an inner layer 36, as shown in FIG. 4. The outer layer 34 preferably comprises a non-woven fabric of synthetic fibers having many thread loops on its surface. The shield 32 is sandwiched between the outer layer 34 and inner layer 36, and the outer and inner layers are secured together such as by stitching along their perimeters. The inner layer 36 preferably comprises a fabric that is breathable and comfortable against the arm. For instance, the inner layer 36 can comprise a tricot fabric or the like. The inner layer preferably has sufficient thickness to provide padding between the arm and the shield 32.

Based on the foregoing, it will be appreciated that the invention enables a medical practitioner to draw medication from one or more vials without having to touch the non-sterile outside surfaces of the vial(s) with his or her gloved hands. In this manner, the sterility of the practitioner's gloves is not compromised, and no assistant is required for holding the vial as is the current practice in many cases.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A wearable vial holder for securing at least one vial of medication on the person of a medical practitioner, the wearable vial holder comprising:
   a body-engaging member structured and arranged to be secured to a part of the body of a medical practitioner; and
   a vial gripper affixed to the body-engaging member for releasably grasping and holding at least one vial in a position having a cap of the vial accessible so that the practitioner has access to the at least one vial for one-handed drawing of medication therefrom using a syringe with a needle, the vial gripper being structured and arranged to releasably grasp and hold vials of various capacities including vials containing up to at least about 50 ml of liquid medication.

2. The wearable vial holder of claim 1, wherein the body-engaging member includes a needle-puncture-resistant shield for covering the body of the medical practitioner to prevent accidental needle sticks.

3. The wearable vial holder of claim 2, wherein the needle-puncture-resistant shield comprises a flexible sheet and is sandwiched between an inner layer and an outer layer of the body-engaging member.

4. The wearable vial holder of claim 3, wherein the inner layer is a breathable fabric.

5. The wearable vial holder of claim 1, wherein the body-engaging member has an outer surface that defines a first component of a two-component releasable fastening system, and wherein the vial gripper includes a gripping member affixed to the body-engaging member, the gripping member having a surface that defines a second component of the two-component releasable fastening system such that a vial is secured in the vial gripper by disposing the vial between the gripping member and the body-engaging member and releasably attaching the gripping member to the outer surface of the body-engaging member by mutual engagement of the two components of the fastening system.

6. The wearable vial holder of claim 5, in combination with a vial having an attachment member affixed thereto, the attachment member having a surface defining the second component of the two-component releasable fastening system, whereby the vial is releasably attached to the body-engaging member via the attachment member on the vial and is further secured by the gripping member.

7. The wearable vial holder of claim 6, wherein the two-component fastening system comprises a hook and loop system.

8. The wearable vial holder of claim 7, wherein the attachment member and the gripping member comprise hook components of the hook and loop system and the outer surface of the body-engaging member comprises a loop component of the hook and loop system.

9. The wearable vial holder of claim 1, wherein the body-engaging member is structured and arranged to be wrapped around and secured to an arm of a medical practitioner.

10. The wearable vial holder of claim 9, wherein the body-engaging member includes at least one elastic member.

11. The wearable vial holder of claim 10, wherein the body-engaging member includes a shield portion forming a needle-puncture-resistant shield that wraps at least partway about the arm and is secured in place by the at least one elastic member.

12. The wearable vial holder of claim 11, wherein the at least one elastic member comprises a first elastic member having at least one end releasably attachable to the shield portion in various positions for adjusting a fit of the wearable vial holder about the arm.

13. The wearable vial holder of claim 12, wherein the at least one elastic member comprises a second elastic member having opposite ends non-releasably affixed to the shield portion to form an arm-encircling structure that holds the wearable vial holder in place on the arm while the first elastic member is adjusted.

14. The wearable vial holder of claim 11, wherein the shield portion and the at least one elastic member on outer surfaces thereof have a first component of a releasable hook and loop fastening system, and the vial gripper comprises a strap on one surface of which is a second component of the hook and loop fastening system for releasably affixing the strap in various positions to at least one of the shield portion and the elastic member.

15. A wearable vial holder for releasably securing at least one vial of medication in a substantially fixed position with respect to the body of a medical practitioner, the wearable vial holder comprising:

a body-engaging member structured and arranged to be secured to a part of the body of a medical practitioner, the body-engaging member including a shield portion that is needle-puncture-resistant to protect the practitioner against accidental needle sticks, a surface of the body-engaging member having a first component of a releasable hook and loop fastening system; and a vial gripping strap affixed to the shield portion for releasably grasping and holding at least one vial on the shield portion so that the practitioner has access to the at least one vial for one-handed drawing of medication therefrom using a syringe with a needle, a surface of the strap having a second component of the hook and loop fastening system such that the strap is releasably attachable to the shield portion in various positions to accommodate various sizes and numbers of vials, the vial gripping strap being structured and arranged to releasably grasp and hold vials of various capacities including vials containing up to at least about 50 ml of liquid medication.

16. The wearable vial holder of claim 15, in combination with a vial having an attachment member affixed thereto, the attachment member comprising the second component of the hook and loop fastening system, whereby the vial is releasably attached to the body-engaging member via the attachment member on the vial and is further secured by the gripping strap.

17. The wearable vial holder of claim 15, wherein the shield portion comprises a multi-layered structure including at least a shield layer of needle-puncture-resistant material and an outer layer providing the first component of the hook and loop fastening system.

18. The wearable vial holder of claim 17, wherein the shield portion further comprises an inner layer of breathable material for placement against the body of a medical practitioner.

* * * * *